United States Patent [19]

Chau

[11] 4,348,374

[45] Sep. 7, 1982

[54] CHARCOAL COATED ADSORBENT DEVICE

[75] Inventor: Kue H. Chau, Mundelein, Ill.

[73] Assignee: Abbott Laboratories, North Chicago, Ill.

[21] Appl. No.: 900,455

[22] Filed: Apr. 27, 1978

Related U.S. Application Data

[63] Continuation-in-part of Ser. No. 833,791, Sep. 16, 1977, abandoned.

[51] Int. Cl.$^3$ .................. G01N 33/54; G01N 33/56; G01N 23/06
[52] U.S. Cl. .................. 424/1; 23/230 B; 422/71; 424/12
[58] Field of Search .............. 424/1, 8, 12; 23/230 B, 23/259

[56] References Cited

U.S. PATENT DOCUMENTS 3,928,553  12/1975  Hollander ..................... 424/1

Primary Examiner—Christine M. Nucker
Attorney, Agent, or Firm—Steven M. Odre

[57] ABSTRACT

A charcoal coated solid support of regular geometric form can be employed as an adsorbent device in a variety of biochemical assays to adsorb selected components for separation and easy removal from an assay medium.

5 Claims, No Drawings

CHARCOAL COATED ADSORBENT DEVICE

CROSS REFERENCE TO RELATED APPLICATION

This application is a continuation-in-part of my prior application Ser. No. 833,791, filed Sept. 16, 1977, now abandoned.

BACKGROUND OF THE INVENTION

When assaying the binding of ligands to proteins it is often necessary to separate the ligand into proteinbound and unbound (free) fractions in order to determine quantities or perform measurements on specific fractions. The separation can be effected with ultrafiltration and gel filtration; selective precipitation of protein together with the bound ligand such as precipitation with ammonium sulfate, polyethylene glycol or a second antibody; selective adsorption of the free ligand by an adsorbent such as a suspension of activated charcoal or ion exchange resin; or a solid support phase on which the binding proteins or adsorbents are immobilized such as antibody coated tubes and resin sponges.

Various adsorption techniques and applications are demonstrated by the following references:

Herbert, U.S. Pat. No. 3,442,819 teaches that charcoal coated with a molecular sieve which will prevent large molecules of complexes from reaching and adhering to the carbon can be used to separate components in biochemical assays by adsorbing particular molecules. The selection of coating material permits the selective adsorption of one compound from another, i.e., generally molecules smaller than the pore size of the molecular sieve will pass through the sieve and be adsorbed, whereas, the molecules as large or larger than the sieve will not pass through the sieve and will remain in the assay medium.

Shannon, et al., U.S. Pat. No. 3,947,564 demonstrates the separation of thyroxine from serum proteins by the adsorption of thyroxine onto a montmorillonite clay in acid solution with subsequent centrifugation.

Lewin, et al., U.S. Pat. No. 3,937,799 illustrates the adsorption of unbound vitamin B-12 from an assay medium using a premeasured tablet of bentonite.

Applicant is also aware of a commercially available filtration device marked by Isolab which utilizes charcoal that has been bound to a polyethylene support. This adsorbent reagent is granular and amorphous. As a result, there is a variable amount of charcoal on each particle. Employing this reagent requires measuring by weight or volume to disperse the desired amount for each use. Usually, the reagent is packed in a column to be used as a filtration or chromatographic device. It is alleged that the advantage of the plastic support is that it enhances the flow rate of fluid through the column by preventing the charcoal from packing tightly.

SUMMARY OF THE INVENTION

Applicant has developed an advanced design, activated charcoal-coated, solid support, adsorbent device fashioned in a regular geometric foam which is useful for the separation of ligands by adsorption from proteinacious material in an assay medium. The device presents a uniform, convenient, premeasured, easily separated form of activated charcoal which obviates the inconvenience of working with charcoal columns and slurries and completely eliminates measuring the separation medium, filtration and centrifugation. This invention is also concerned with the method of separating ligands by the use of the disclosed adsorbent device.

DESCRIPTION OF THE PREFERRED EMBODIMENT

Applicant has found that a solid support structure of regular geometric form, coated with very fine particles of activated charcoal, can be introduced into an assay medium, incubated until a sufficient quantity of unbound ligands have attached and removed from the medium so that the adsorbed ligands can be measured or analyzed.

Almost any easily manipulated solid structure of uniform size and regular geometric shape can be employed as a support for the charcoal coating to insure accurate assays. Also, since the support is to be coated with charcoal, its composition is not of primary importance. However, applicant has found it preferable to use a lightweight plastic structure that can be fabricated, molded or extruded into a regular geometric form such as a sphere, bead, cylinder or cube of convenient size to function easily within the confines of test tubes containing the assay medium. Any of the commonly available polymeric plastics such as polystyrene, polyurethane, polypropylene or the like would be suitable as the support structure. Although these plastics could be molded or extruded into any desired shape, it has been found that a spherical bead of about 0.6 to 0.8 centimeters in diameter is the most convenient for use in the assay medium. It has also been found that the surface of the bead should be abraded or roughened. This may be done either chemically or physically. Although a rough surface is not required, applicant has found that this will enhance the adherence of the charcoal.

The actual coating of the sphere is performed by preparing a slurry of charcoal in water, adding the slurry to a quantity of beads or solid supports and agitating over a period of time until all the beads are uniformly coated with an adequate quantity of charcoal particles. At the end of agitation, excessive and loose charcoal particles are washed from the bead surface and the wet beads are dried with warm air.

The surface area and particle size of commercially available activated charcoal can vary greatly, but most pulverized grades can be employed as a satisfactory source of coating material for this device. The selection of charcoal, of course, depends on the chemical property of the ligand and the composition of the assay medium. Best results, however, have been obtain-d using activated charcoal in which at least 80% of the particles pass through a #325 screen mesh.

The amount of activated charcoal employed in the coating process will depend on the number of beads to be coated. Applicant has found no advantage to imparting a thick charcoal coating to the beads. Coating only the surface of the bead has produced satisfactory results.

Commercially, the coating can be performed in the revolving coating pans or forced air columns commonly used for coating tablets. The following example illustrates a typical commercial coating process.

EXAMPLE I

Charcoal Coated Beads

A revolving coating pan is loaded with 27.5 kg of polystyrene beads 0.7 cm diameter. In another container containing 40 liters of water for irrigation, 6 kg of activated charcoal is added slowly with stirring to avoid splashing of fine particles. This slurry is mixed well for about onehalf hour and then transferred to the revolving coating pan. The pan is rotated at a speed of 22–26 rpm for a period of 18 hours. The beads are then air dried at a temperature of about 45° C. for a period of about 30 minutes. Finally, the coated beads are removed from the coating pans and stored in plastic-bag lined drums.

As mentioned previously, these charcoal coated beads are particularly useful for the adsorption of unbound ligands from an assay medium. The following describes an assay of Liothyronine binding to serum proteins, which utilizes the claimed charcoal coated beads.

Thyroxine is bound by at least three different proteins in serum. These are: thyroxine binding globulin (TBG), to which binding is the strongest; prealbumin, to which binding is of intermediate affinity; and albumin, to which binding is relatively weak. Liothyronine (triiodothyronine) is similarly but less firmly bound to thyroxine binding globulin and albumin. In hyperthyroidism, the primary thyroxine binding sites are nearly saturated. Therefore, added liothyronine $^{125}$I is taken up by the secondary binding sites such as the charcoal bead. In hypothyroidism, it is the primary sites (relatively unsaturated) which take up added liothyronine $^{125}$I. In short, the binding or uptake by the bead is increased in hyperthyroidism and decreased in hypothyroidism. Uptake is also decreased in normal pregnancy, consistent with the increase of thyroxine binding protein which occurs.

The percentage of bead uptake, while not translatable into definitive units of weight of thyroxine or liothyronine, is an indication of thyroid function since it shows how much excess binding capacity the serum TBG has available. The greater the capacity, the greater the uptake of lableed liothyronine and the smaller the amount of radioactive liothyronine available for bead adsorption. In hypothyroidism the serum thyroxine or liothyronine is present in smaller than normal amounts and the bead uptake will be small since the serum TBG will bind more of the added radioactive material. The reverse is true when the patient is hyperthyroid: the bead uptake will be higher since the serum TBG is already more saturated with thyroxine and liothyronine from the serum.

Reagents

1. Liothyronine $^{125}$I Reagent Solution: Radioactive liothyronine in a tris-malate buffer pH 6.9, stabilized with 0.1% gelatin.
2. Polystyrene beads coated with activated charcoal.
3. Reference Control Serum: Human serum having a normal concentration of thyroxine as determined with T4 RIA-PEG and a normal degree of saturation of TBG.

Procedure

After all serum samples and reagents were brought to room temperature, 25 μl of the patient's serum was dispensed by pipette into a properly labeled assay tube. Additionally, 25 μl of the Reference Control Serum was dispensed into two additional properly labeled assay tubes. With a calibrated pipette, 250 μl of Liothyronine $^{125}$I Reagent Solution was added to each tube. No immediate vortexing or mixing was necessary. All tubes were mounted on a shaker and incubated with shaking at room temperature for about 20 minutes.

After agitation and incubation, the tubes are removed from the shaker and the liquid decanted into a container for radioactive liquid waste. The beads and rim of the assay tubes were blotted dry with paper towels. No washing was necessary. The tubes are counted in a suitable scintillation well counter for one minute (or until 10,000 counts accumulate). The count rate was recorded in net counts per minute and the value of the patients serum was calculated.

A radioimmunoassay employing a charcoal-coated solid support can be demonstrated by the following example in which the ligand T3 is to be assayed.

EXAMPLE II

Twenty-five microliters of each six standard sera were added to each of twelve tubes labeled in duplicate to indicate 0, 0.5, 1.0, 2.0 and 8.0 ng/100 ml of T3. Twenty-five microliters of the specimen to be assayed were also added to appropriately labeled tubes. Fifty microliters of reagent containing liothyronine labeled with $^{125}$I and a suitable blocking agent such as ANS was added to both the standard and unknown serum solutions. Two hundred microliters of liothyronine antiserum (rabbit) was also added to each tube and the contents were mixed well. All tubes were incubated at room temperature for two hours. Following the incubation period, one activated charcoal-coated bead was added to each tube. The tubes and contents were then agitated in a shaker for 20 minutes. The liquid was aspirated from each tube leaving the charcoal-coated bead which was then measured in a scintillation counter for the radioactivity. From this it was possible to calculate the percentage of bound antigen for each bead, to plot the average percentage bound antigen for each standard serum vs. the corresponding liothyronine concentration of the patient specimen.

An enzyme immunoassay can also demonstrate the use of a charcoal-coated solid support for the separation of protein bound and unbound ligands.

EXAMPLE III

Fifty microliters of a reagent solution containing 0-dianisidine-cortisol and ANS was added to each labeled tube containing 25 μl aliquots of standard sera or or unknown specimens. Two hundred microliters of cortisol antiserum was added to the contents of each tube and the contents were mixed well. The tubes were incubated at room temperature for two hours. Following the incubation period, one activated carcoal-coated bead was added to each tube and the contents were agitated in a shaker for 20 minutes. The liquid was then aspirated from each tube and 0.2 ml of hydrogen peroxide and 0.1 ml of horseradish peroxidase reagent was added to each bead. The enzyme activity was measured with a spectrophotometer at 460 mm at 15 second intervals for 10 minutes. The changes in adsorbance of the standard sera and specimens were compared to quantify the concentration of cortisol in the specimens.

Although the invention has been described with reference to various specific examples and embodiments, it should be realized that the invention is not so limited but that it can be demonstrated within the scope of the following claims.

What is claimed is:

1. An adsorbent device for the separation of ligands from an assay medium by adsorption which comprises a solid support of regular geometric form coated with activated charcoal.

2. An adsorbent device according to claim 1 which is spherically shaped.

3. A method for the separation of ligands from an assay medium which comprises adsorbing the ligands onto the adsorbent surface of an activated charcoal-coated solid support of regular geometric form.

4. A method according to claim 3 wherein the solid support is spherically shaped.

5. A ligand binding assay for proteins in a physiological fluid which comprises:
   a. introducing an aliquot of the specimen to be assayed into a vial containing a labeled ligand and an activated charcoal-coated solid support of regular geometric form;
   b. allowing the contents of the vial to incubate;
   c. separating the solid phase containing unbound ligands adsorbed on the activated charcoalcoated solid support from the liquid phase containing protein bound ligand; and
   d. determining the quantity of labeled ligand in either phase which is a function of the degree of ligand binding in the sample fluid.

* * * * *